(12) United States Patent
Stasz et al.

(10) Patent No.: US 6,485,432 B1
(45) Date of Patent: Nov. 26, 2002

(54) PYRO/PIEZO SENSOR WITH ENHANCED SOUND RESPONSE

(75) Inventors: Peter Stasz, St. Paul; William H. Ham, Mound; Michael W. Barr, Deep Haven; Sheri L. Brewer, Lino Lakes; Joseph D. Vallie, Vadnais Heights, all of MN (US)

(73) Assignee: Dymedix, Corp., Minneapolis, MN (US)

( * ) Notice: Subject to any disclaimer, the term of this patent is extended or adjusted under 35 U.S.C. 154(b) by 0 days.

(21) Appl. No.: 09/712,506

(22) Filed: Nov. 14, 2000

(51) Int. Cl.⁷ .................................................. A61B 5/08
(52) U.S. Cl. ...................... 600/532; 600/529; 600/534; 600/537; 600/586
(58) Field of Search .............................. 600/529, 532, 600/534, 537, 552, 555, 586; 310/800; 73/862.68

(56) References Cited

U.S. PATENT DOCUMENTS

| | | | |
|---|---|---|---|
| 4,814,661 A | * 3/1989 | Ratzlaff et al. | 310/328 |
| 5,099,702 A | * 3/1992 | French | 73/862.68 |
| 5,311,875 A | * 5/1994 | Stasz | 600/537 |
| 5,913,829 A | * 6/1999 | Reeves et al. | 600/528 |
| 6,254,545 B1 | * 7/2001 | Stasz et al. | 600/529 |

* cited by examiner

Primary Examiner—Kevin Shaver
Assistant Examiner—Patricia Mallari
(74) Attorney, Agent, or Firm—Nikolai & Mersereau P.A.

(57) ABSTRACT

A combination thermal and vibration sensor for use in sleep monitoring equipment comprises a thin film of plastic exhibiting both pyroelectric and piezoelectric properties. By providing a layer of foam material covering only a predetermined portion of one major surface of the film layer, it is found that the thermal mass of the sensor is changed to the point where the pyroelectric signal can be more readily isolated from the piezoelectric signal using conventional signal processing techniques. Because the layer of foam material is not present on a remaining portion of the piezo/pyro film, the signal output due to the film's piezoelectric properties is not unduly dampened and attenuated.

14 Claims, 4 Drawing Sheets

PYRO/PIEZO SENSOR WITH ENHANCED SOUND RESPONSE

BACKGROUND OF THE INVENTION

I. Field of the Invention

This invention relates generally to electronic sensors for monitoring both temperature change and sound using a single transducer, and more particularly to the construction of such a sensor that more readily allows the temperature signal to be separated from the sound signal using conventional signal processing techniques, e.g., filtering, and which provides a more robust output due to sound vibrations.

II. Discussion of the Prior Art

In the U.S. Pat. No. 5,311,875, which is hereby incorporated by reference, there is described a system for electronically monitoring breathing patterns and may find use as a sleep sensor in a hospital sleep lab. The system described therein utilizes a plastic film exhibiting both pyroelectric and piezoelectric properties, such as a polyvinylidene fluoride (PVDF) film. The film transducer has a conductive electrode on opposed major surfaces thereof and electrical wires connect the electrodes to an electronics module that is designed to separate the transducer output into two separate channels, one being for temperature and the other being for sound or vibration.

As is explained in copending application Ser. No. 09/416,660, filed Oct. 12, 1999, assigned to the assignee of the present invention and which application is hereby incorporated by reference, testing performed by the assignee of the present invention has shown that the signal proportional to temperature variation greatly exceeds that due to noise or vibration by a factor of about 50:1. The temperature-related signal also and is rich in frequency components in the 20 Hz to 50 Hz range during normal exhalation. These properties of earlier sensor designs have caused a difficulty in preventing the thermal component of the transducer from crossing over into the sound channel, often leading to the occurrence of false positives when both sound signals and temperature signals were being simultaneously monitored. The aforereferenced '660 application describes a solution to the problem. By increasing the thermal mass of the sensor, the effective rise-time of the thermal signal can be greatly reduced, while not attenuating the signal amplitude occasioned by sound/vibration of the sensor below a detectable level.

As is further described in the aforereferenced '660 application, the thermal mass of the PVDF transducer can be tailored by affixing a layer of plastic foam material onto the transducer film. The plastic foam material is made coextensive with the area of the PVDF film, i.e., it covered the entire surface of the PVDF film.

While the invention described in the aforereferenced '660 application resulted in a significant improvement in the performance of the sensor in terms of being able to tailor the rise-time of the thermal signal in relation to the thickness of the foam plastic material applied, it did result in some loss of sensitivity of the transducer to sound/vibration signals.

It is, therefore, a principal object of the present invention to provide an improved pyro/piezo PVDF film transducer having a slower rise-time of the thermal signal to the point where it no longer overlaps with the predominant frequency components of the piezo or sound signal, but where the vibration/sound signal is not unduly attenuated.

SUMMARY OF THE INVENTION

In accordance with the present invention, control over the thermal mass of the transducer described in the aforereferenced Stasz '875 patent is achieved by affixing a layer of plastic foam material unto the transducer film on at least one surface thereof but where the foam layer need not be coextensive with the PVDF film layer, thus leaving a portion thereof undamped by the plastic foam material. Thus, in accordance with the preferred embodiment of the present invention, the combination thermal and vibratory sensor comprises a plastic film exhibiting pyroelectric and piezoelectric properties and has a predetermined shape configuration with first and second major surfaces. A thin layer of conductive material is disposed on and is coextensive with the first and second major surfaces. A pair of elongated conductors are individually attached at one end thereof to the conductive material on the first and second major surfaces. A layer of a material for changing the thermal mass of the sensor is adhered to the layer of conductive material on at least one of the first and second major surfaces so as to overlay only a predetermined portion of the one major surface while leaving the remainder of that one major surface free of the layer of material. In use as a sleep sensor, the transducer of the present invention may be adhered to the upper lip of a person such that inspiratory and expiratory air flow, via the nasal passages, impinges primarily on the portion of the sensor to which the plastic foam material is adhered while the remainder portion of the transducer that is free of foam material either extends beyond the lips and over the mouth or engages the base of the nasal septum. Noise and vibration which may be caused by a person's snoring remains undamped, allowing the film to output a more robust piezoelectric signal.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
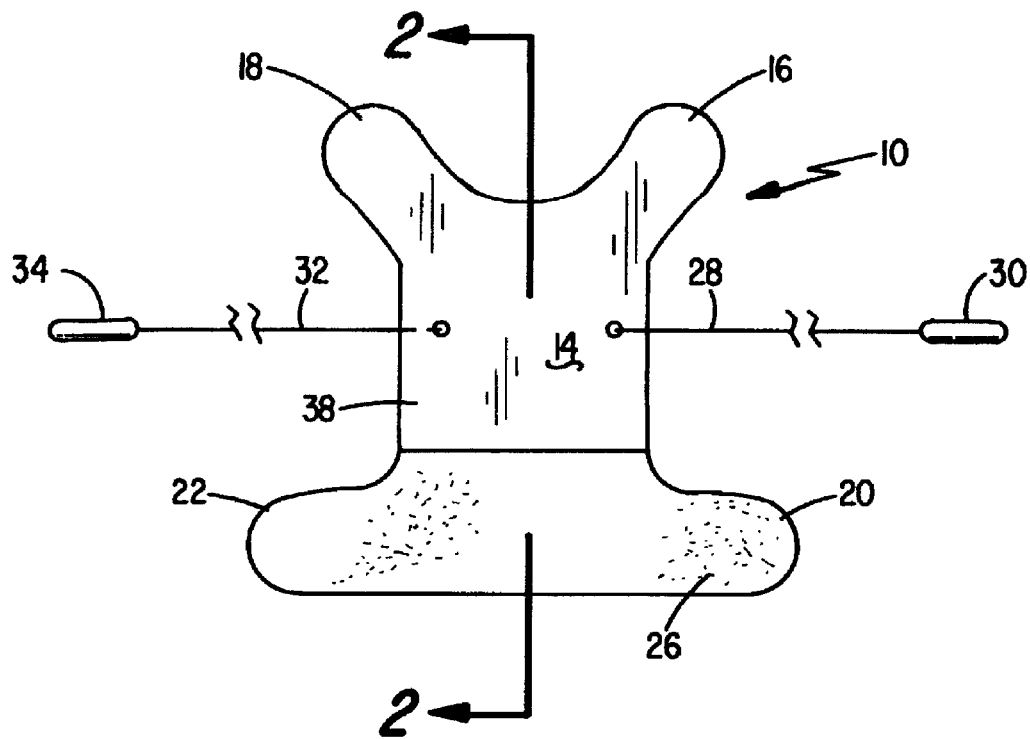
FIG. 1 is a front plan view of a pyro/piezo sensor constructed in accordance with the present invention.

Referring to FIG. 1, there is indicated generally by numeral 10 a transducer element especially designed for use in sleep pattern analysis equipment and constructed in accordance with a first embodiment of the present invention. It comprises a laminated construction having as its active element a layer of plastic film 12 which exhibits both pyroelectric and piezoelectric properties. A polyvinylidine fluoride (PVDF) film, whose thickness may range from about 0.5 to about 5 mils is preferred. The film 12 and the layers laminated therewith, and yet to be described in detail, are cut so as to provide a preferred shape like that illustrated in the plan view of FIG. 1. As is shown, the sensor or transducer 10 includes a generally rectangular midsection 14 with integrally formed, obliquely extending rounded arms 16 and 18 that project from a first end edge of the rectangular midsection 14 along with integrally formed, laterally extending rounded legs 20 and 22 projecting from a second end edge of the rectangular midsection 14.

Figure 2:
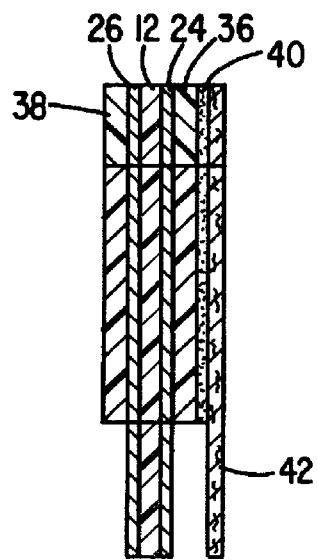
FIG. 2 is a side elevation view of the sensor of FIG. 1.

Examination of the cross-sectional view of FIG. 2 shows that the centrally disposed PVDF film layer 12 has its opposed major surfaces coated with layers 24 and 26, each being a conductive material sufficiently thin that it can readily flex without cracking. Layers 24 and 26 may comprise carbon coatings on the PVDF film, but conductive materials other than carbon may also be utilized. The layers 24 and 26 constitute electrodes attached to the PVDF film 12.

An elongated flexible conductor 28 electrically connects to the layer 26 and includes a connector 30 at its proximal end that is adapted to be attached to a signal receiver module (not shown). In a similar fashion, an elongated flexible conductor 32 connects to the conductive layer 24 on the opposite side of the film layer 12 and it, too, has a connector 34 adapted to attach to the receiver module.

Adhesively bonded onto the conductive layer 26 is a layer of plastic foam material 36 which, in accordance with the aforereferenced '666 application, functions to change the thermal mass of the sensor 10. However, unlike the sensor disclosed in the '666 application, in accordance with the present invention, the plastic foam layer 36 is not coextensive with the film layer 12, but instead, covers only a predetermined portion of the transducer film material. More particularly, and as best seen in FIG. 1, the layer of plastic foam 36 only covers the generally rectangular midsection 14 and the obliquely projecting rounded arms 16 and 18, leaving the laterally extending rounded legs 20 and 22 uncovered.

A further layer of plastic foam material 38 is adhesively secured to the conductive layer 24 and it has the same shape configuration as the foam layer 36. It can, therefore, be seen that only a predetermined portion of the major surfaces of the metallized film layer 12 has the foam layers 36 and 38 affixed thereto with the remainder of the film layer being free of the foam layer.

Without limitation, the overall length dimension of the sensor for use on adults may be about 1.25 inch including the obliquely extending rounded arms and the laterally extending rounded leg portions. The width of the leg portion may be about 1.4 inch with the radius of the curved ends being about 0.25 inch. The generally rectangular midsection may measure 0.4 inch in height and 0.7 inch in width. The overall thickness of the sensor will be about 0.10 inch where the foam layers are present but only about 0.005 inch in the remaining portion where only the film thickness is involved.

The sensor 10 is especially designed so as to be attached to the upper lip of a person during the course of a respiratory analysis, such as in a sleep lab. As such, the film layer 36 may be provided with a layer of skin compatible, pressure sensitive adhesive 40 which, prior to use, may be shielded from contamination by a layer 42 of release paper. The release paper 42 is, of course, stripped from the transducer at the time of application to expose the adhesive layer 40.

In use, the sensor 10 is attached to the patient's upper lip with the rounded arms 16 and 18 directly below the nasal openings and the dimensions are such that the laterally extending leg portions 20 and 22 will extend over the edge of the upper lip so as to overlay the mouth opening. The portion of the sensor overlaying the mouth opening, being void of plastic foam material is more directly responsive to sound vibrations occasioned by episodes of snoring and, therefore, capable of producing a more robust piezoelectric response than when the entire transducer is foam covered.

Figure 3:
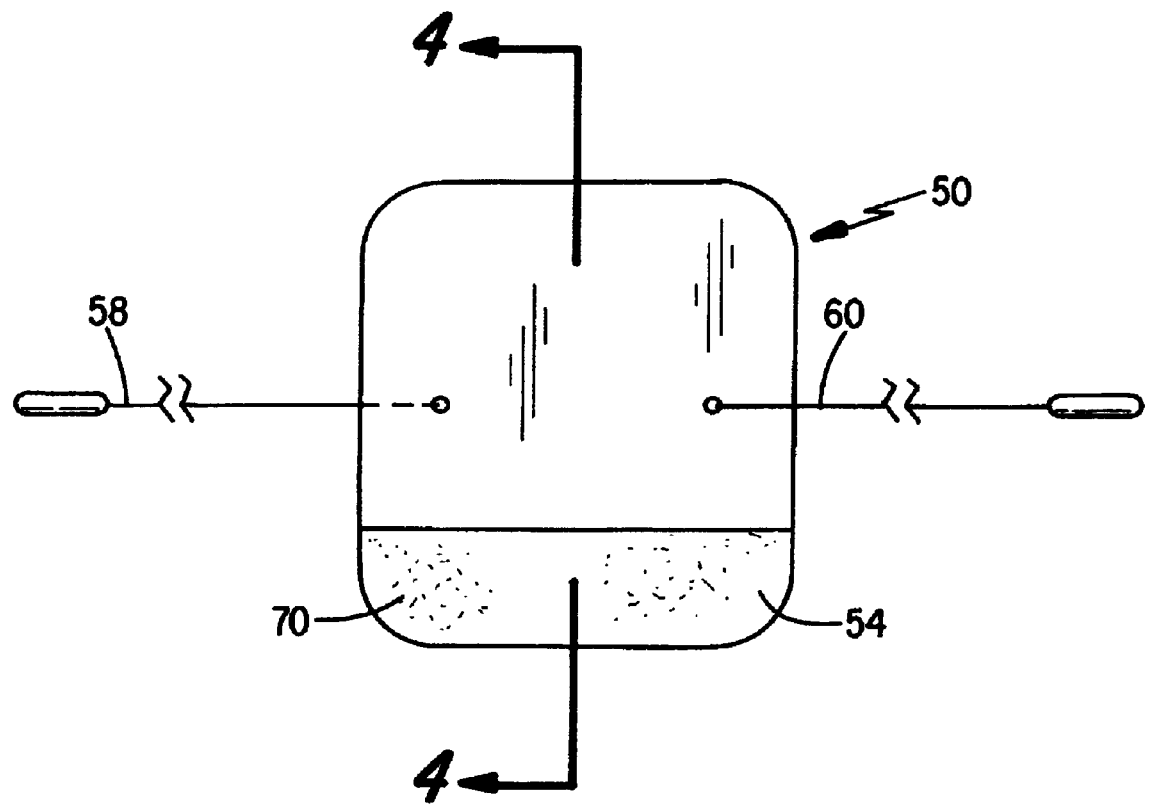
FIG. 3 is a front plan view of a pyro/piezo sensor constructed in accordance with an alternative embodiment of the invention.
Figure 4:
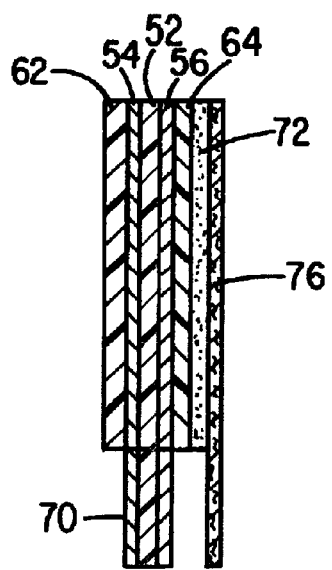
FIG. 4 is a side elevation view of the sensor of FIG. 3.

The embodiments of FIGS. 3 and 4 show an adaptation of the present invention to a breathing sensor for newborns and small infants. It is indicated generally by numeral 50 and in the plan view is generally rectangular, but having rounded corners. Without limitation, the height dimension may be approximately 0.55 inch and the length dimension 0.515 inch. The rounded corners may have a radius of ⅛ inch.

In the cross-sectional view of FIG. 4, the PVDF film layer 52 has conductive electrodes 54 and 56 on opposed major surfaces thereof and they are coextensive with those major surfaces. First and second elongated conductive leads 58 and 60 are individually connected at a first end thereof to the conductive layers 54 and 56 and adhesively bonded to the conductive layers are layers 62 and 64 capable of changing (increasing) the thermal mass of the sensor. The layers 62 and 64 are preferably not coextensive with the film layer 52, but instead, only overlay a predetermined portion of the PVDF film layer, leaving the remainder free of such material. A workable sensor can be realized, however, by making only foam layer 62 coextensive with the film layer. Again, it is intended that the transducer illustrated in FIG. 3 be adhesively affixed to the newborn's upper lip and, in this regard, a layer of non-irritating, skin compatible, medical-grade adhesive 72 is applied to the exposed surface of foam layer 64 and that adhesive layer is shielded by a release paper 76 until just prior to its application to the infant.

While in the embodiments illustrated, a layer of foam plastic material is disposed on each of the major surfaces of the PVDF film layers, the invention can also be implemented with a single layer of plastic foam, such as foam layer 36 in the embodiment of FIG. 2 and plastic foam layer 62 in the embodiment of FIG. 4. In such an arrangement, the adhesive for adhering the transducer to the subject's upper lip would be applied directly to one major surface of the conductive layer, i.e., the major surface not having the foam layer adhered to it.

When the transducer patch of FIG. 3 is affixed to an infant or newborn, inspiratory and expiratory gases passing through the infant's nasal orifices will impinge upon the portion of the transducer 50 carrying the plastic foam layer 62 whereas the lower portion 70 that is free of any plastic foam material overlaying the infant's mouth will sense the air being inhaled and exhaled through the mouth. During inspiratory flow, the affected portion of the transducer will have relatively cool ambient temperature air pass over it while during expiratory flow, the air impinging on the transducer will be higher—about body temperature. Thus, with normal breathing, the output signal from the transducer should vary rhythmically. However, if coughing, choking or noises attributed to partially occluded air passages should occur, the transducer will output a signal based upon its piezoelectric properties. Because the portion 70 of the transducer 50 does not carry the foam material used to modify the thermal mass, the transducer is capable of producing a more robust signal related to sound and vibration.

Figure 5:
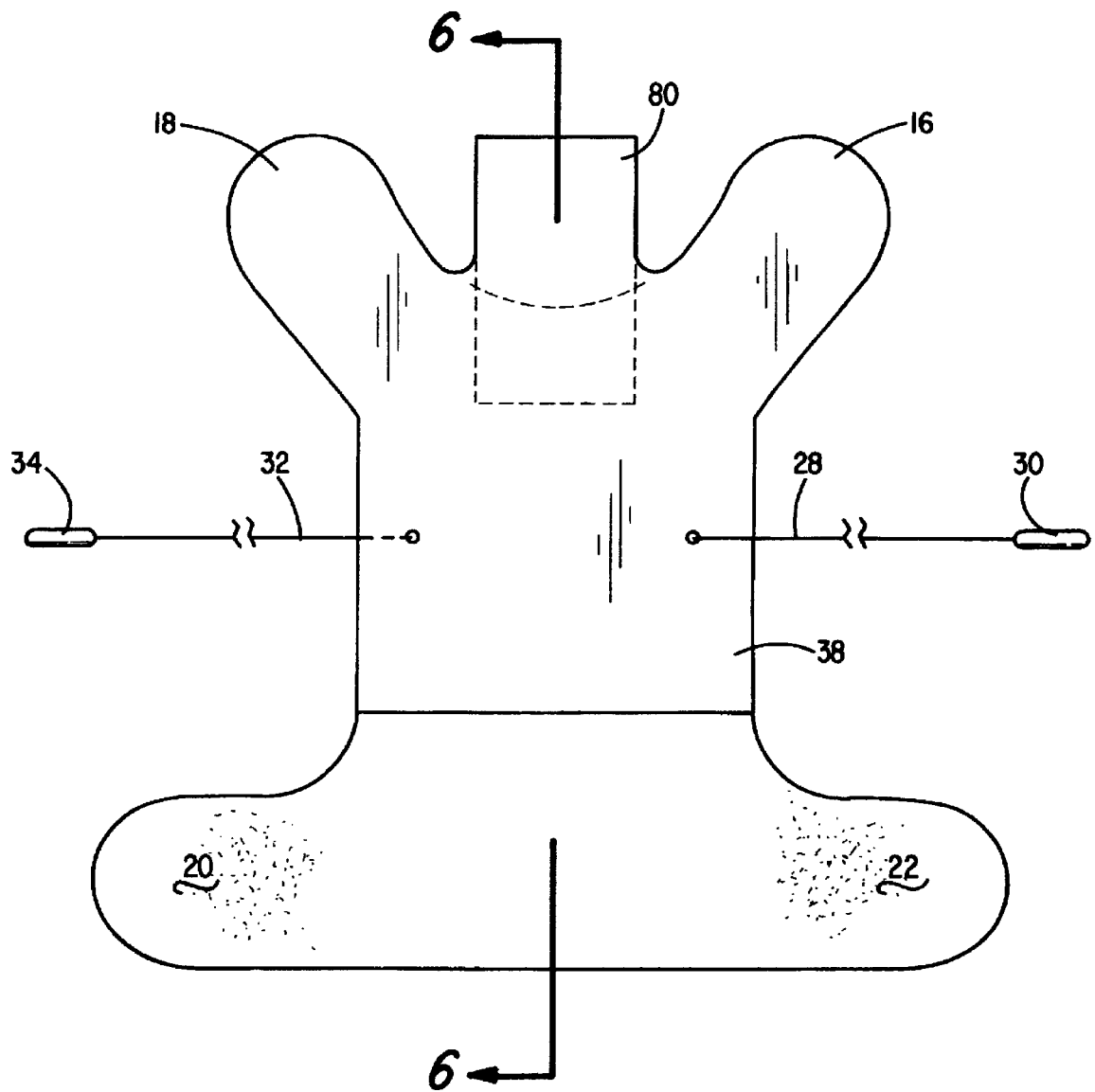
FIG. 5 is a plan view of a further alternative embodiment of the invention.
Figure 6:
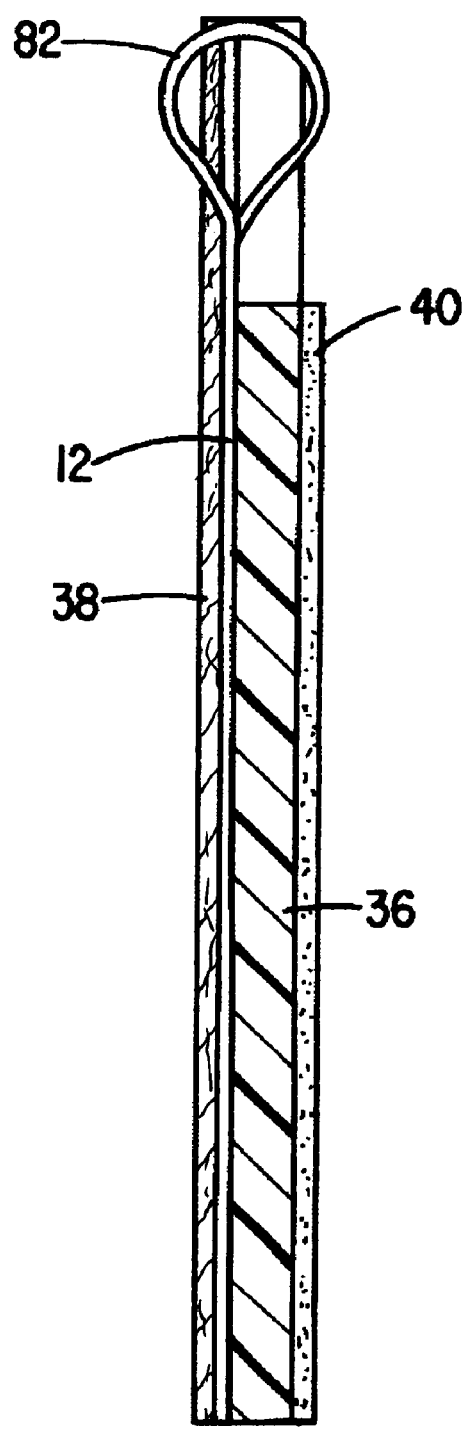
FIG. 6 is a cross-sectional view taken along line 6—6 in FIG. 5.

FIGS. 5 and 6 illustrate yet another embodiment of the pyro/piezo sensor of the present invention which is designed to enhance its sound response. The device is similar in shape to the embodiment or FIG. 1, but instead of leaving the laterally extending legs 20 and 22 devoid of plastic foam, the plastic foam layers 36 and 38 extend over the laterally extending legs. The PVDF film layer 12 is cut so to provide a generally rectangular tab 80 that extends outward between the obliquely extending arms 16 and 18 and which is folded back upon itself to form a loop 82 as best seen in the cross-sectional view of FIG. 6. A layer of pressure-sensitive, skin-compatible adhesive 40 is again adhered to the foam layer 36 to facilitate attachment of the sensor to an upper lip of a person. As with the embodiment of FIG. 1, the obliquely extending arms 16 and 18 will be positioned directly in line with the user's nasal openings and the loop 82 is designed to press against the base of the nasal septum. When thusplaced, the laterally extending legs 20 and 22 overhang the upper lip and subtend the wearer's mouth and the loop is in a dead zone relative to inspiratory and expiratory air flow.

The positioning of the loop 82 and the fact that it is devoid of the foam material 36 results in an enhanced piezoelectric output from the sensor occasioned by the wearer's snoring episodes because it is more intimately in contact with the nasal septum and/or with the skin under the nasal septum where snoring vibrations are more intense.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself

What is claimed is:

1. A combination thermal and vibration sensor comprising:
    (a) a plastic film exhibiting pyroelectric and piezoelectric properties and having a predetermined shape configuration with first and second major surfaces wherein the predetermined shape configuration includes a generally rectangular midsection with integrally formed obliquely extending arms with a loop disposed between said arms, the arms and the loop projecting from a first end edge, and integrally formed laterally extending legs projecting from a second end edge;
    (b) a thin layer of conductive material disposed on and coextensive with the first and second major surfaces;
    (c) first and second elongated conductive leads individually connected at a first end thereof to the conductive material on the first and second major surfaces; and
    (d) a layer of a material for changing the thermal mass of the sensor adhered to the layer of conductive material on at least one of the first and second major surfaces so as to overlay only a predetermined portion of the at least one major surface and leaving said loop free of the layer of material for changing the thermal mass.

2. The combination thermal and vibration sensor of claim 1 wherein the predetermined shape configuration permits placement against an upper lip of a person with the predetermined portion of the one major surface to which the material for changing the thermal mass is adhered is exposed to inspiratory and expiratory nasal air flow.

3. The combination thermal and vibration sensor of claim 2 wherein the layer of material for changing the thermal mass is adhered to the layer of conductive material on both of the first and second major surfaces so as to overlay only a predetermined portion of both of the first and second major surfaces and leaving the remainder of the first and second major surfaces free of the layers of material for changing the thermal mass.

4. The combination thermal and vibration sensor of claim 1 wherein the predetermined shape configuration includes a generally rectangular midsection with integrally formed obliquely extending arms projecting from a first end edge and integrally formed laterally extending legs projecting from a second end edge, the integrally formed laterally extending legs comprising said remainder of the one major surface that is free of the layer of material for changing the thermal mass.

5. The combination thermal and vibration sensor of claim 1 wherein the predetermined shape configuration is generally rectangular but with rounded corners, said predetermined portion comprising about three quarters of the area of the one major surface.

6. The combination thermal and vibration sensor of claim 1 wherein the material for changing the thermal mass is foamed plastic.

7. The combination thermal and vibration sensor of claim 1 wherein the material for changing the thermal mass includes a pressure sensitive adhesive thereon for securing the sensor to a person's skin; and a layer of peel-away release paper covering the adhesive prior to its application to the person's skin.

8. The combination thermal and vibration sensor of claim 7 wherein a portion of said loop presses against a base of the nasal septum and said arms are aligned with the nasal openings when the sensor is adhesively secured to a person's upper lip.

9. A combination thermal and vibration sensor, comprising:
    (a) a layer of polyvinylidene fluoride (PVDF) film having first and second major surfaces of a predetermined shape configuration exhibiting a generally rectangular midsection with obliquely extending spaced-apart lobes projecting from a first end edge of the rectangular midsection and a tab forming a loop disposed in the space between said lobes;

(b) a thin layer of conductive material disposed on both the first and second major surfaces to cover at least said lobes and said generally rectangular midsection;

(c) first and second elongated conductive leads individually connected at a first end thereof to the conductive material on the first and second major surfaces; and (d) a layer of a material for changing the thermal mass of the sensor adhered to the layer of conductive material on at least one major surface and coextensive with said lobes and said midsection and leaving said tab forming said loop free of said layer of material for changing the thermal mass.

10. The combination thermal and vibration sensor of claim 9 wherein said predetermined shape configuration is such that said lobes are positioned to intercept inspiratory and expiratory air flow into and from nasal passages of a person and the loop presses against the base of the person's nasal septum when the midsection is adhered to an upper lip of the person.

11. The combination thermal and vibration sensor of claim 10 wherein said loop is generally in a zone that does not intercept the inspiratory and expiratory air flow.

12. The combination thermal and vibration sensor of claim 9 wherein said predetermined shape configuration further includes laterally extending lobes proximate a second end edge of said rectangular midsection.

13. The combination thermal and vibration sensor of claim 12 wherein the layer of conductive material and the layer of material for changing the thermal mass are coextensive with the obliquely extending lobes, the generally rectangular midsection and the laterally extending lobes.

14. The combination thermal and vibration sensor of claim 9 and further including a pressure sensitive adhesive on the layer of material for changing the thermal mass on the at least one major surface for securing the sensor to a person's upper lip.

* * * * *

UNITED STATES PATENT AND TRADEMARK OFFICE
CERTIFICATE OF CORRECTION

PATENT NO.    : 6,485,432 B1
DATED         : November 26, 2002
INVENTOR(S)   : Peter Stasz et al.

It is certified that error appears in the above-identified patent and that said Letters Patent is hereby corrected as shown below:

<u>Column 6,</u>
Line 28, claim 4 should read:
-- 4.   The combination thermal and vibration sensor of claim 1 wherein the integrally formed laterally extending legs are free of the layer of material for changing the thermal mass. --

Signed and Sealed this

First Day of April, 2003

JAMES E. ROGAN
*Director of the United States Patent and Trademark Office*